United States Patent
Linnes et al.

(10) Patent No.: US 12,061,193 B2
(45) Date of Patent: *Aug. 13, 2024

(54) FLUIDIC CONTROL ELEMENTS FOR SIGNAL READOUT ENHANCEMENT IN TWO-DIMENSIONAL PAPER NETWORKS (2DPN)

(71) Applicant: Purdue Research Foundation, West Lafayette, IN (US)

(72) Inventors: Jacqueline Callihan Linnes, West Lafayette, IN (US); Laura Mae Jamicich, Escondido, CA (US); Elizabeth A. Phillips, West Lafayette, IN (US); Kristin M. Byers, Cape Coral, FL (US); Anna Bird, St. Louis, MO (US)

(73) Assignee: Purdue Research Foundation, West Lafayette, IN (US)

(*) Notice: Subject to any disclaimer, the term of this patent is extended or adjusted under 35 U.S.C. 154(b) by 239 days.

This patent is subject to a terminal disclaimer.

(21) Appl. No.: 17/336,858

(22) Filed: Jun. 2, 2021

(65) Prior Publication Data
US 2021/0285942 A1 Sep. 16, 2021

Related U.S. Application Data

(63) Continuation of application No. 15/875,016, filed on Jan. 19, 2018, now Pat. No. 11,047,853.
(Continued)

(51) Int. Cl.
*G01N 33/543* (2006.01)
*B01L 3/00* (2006.01)

(52) U.S. Cl.
CPC ...... *G01N 33/54306* (2013.01); *B01L 3/5023* (2013.01); *B01L 3/527* (2013.01); *G01N 33/54388* (2021.08); *G01N 33/54393* (2013.01); *B01L 3/502746* (2013.01); *B01L 2200/0621* (2013.01); *B01L 2200/10* (2013.01); *B01L 2200/14* (2013.01); *B01L 2200/16* (2013.01);
(Continued)

(58) Field of Classification Search
None
See application file for complete search history.

(56) References Cited

U.S. PATENT DOCUMENTS 9,528,987 B2 12/2016 Yager
2016/0266118 A1 9/2016 Cho

OTHER PUBLICATIONS

Jung et al., "Point of care testing (POCT) diagnostic systems using microfluidic lab-on-a-chip technology", Microelectronic Engineering, 132, available online Oct. 8, 2014, pp. 46-57. (Year: 2015).*
(Continued)

*Primary Examiner* — Rebecca M Giere
(74) *Attorney, Agent, or Firm* — Purdue Research Foundation

(57) ABSTRACT

This invention relates to an improved version of paper-based analytical device and method for chromatographic chemical or immunoassays. Particularly, this present invention discloses a device and a method for reducing smears and improving sharpness and intensity of test sample readout for a multi-step chemical assay or immunoassay by introducing two additional elements, a time-delay pad (2) and a mixer (1), to the conventional two-dimensional paper network device (2DPN).

19 Claims, 9 Drawing Sheets

Related U.S. Application Data

(60) Provisional application No. 62/447,938, filed on Jan. 19, 2017.

(52) U.S. Cl.
CPC ... *B01L 2300/06* (2013.01); *B01L 2300/0816* (2013.01); *B01L 2300/0867* (2013.01); *B01L 2300/087* (2013.01); *B01L 2400/0406* (2013.01)

(56) References Cited

OTHER PUBLICATIONS

Ramachandran et al., "Long-term dry storage of an enzyme-based reagent system for ELISA in point of care devices", Analyst, 2014, 139, pp. 1456-1462. (Year: 2014).*

Gomez, F.A., The future of microfluidic point-of-care diagnostic devices. Bioanalysis (2013) 5(1), 1-3.

Han, K.N., "Three-dimensional paper-based slip device for one-step point-of-care testing" Sci. Rep. 6, 25710; doi: 10.1038/srep25710 (2016).

Wei, X., et al., Target-Responsive DNA Hydrogel Mediated "Stop-Flow" Microfluidic Paper-Based Analytic Device for Rapid, Portable and Visual Detection of Multiple Targets. Anal. Chem. (2015), 87, 4275-428.

Philips, E., et al., Thermally actuated wax valves for paper-fluidic diagnostics. Lab Chip, (2016), 16, 4230.

Fu, E., et al., Two-Dimensional Paper Network Format That Enables Simple Multistep Assays for Use in Low-Resource Settings in the Context of Malaria Antigen Detection. Anal. Chem. (2012), 84, 4574-4579.

Weng, C., et al., Colored wax-printed timers for two-dimensional and three-dimensional assays on paper-based devices. Biomicrofluidics 8, 066502 (2014).

Grant et al., Highly-Sensitive Two-Dimensional Paper Network Incorporating Biotin-Streptavidin for the Detection of Malaria, Analytical Chemistry Technical Note, published Jan. 29, 2016, pp. 2553-2557 (2016).

Shin et al., "Functional Packagin gof Lateral Flow Strip Allows Simple Delivery of Multiple Reagents for Multistep Assays", Analytical Chemistry, 88, p. 10374-10378, published Oct. 5, 2016 (2016).

\* cited by examiner

FLUIDIC CONTROL ELEMENTS FOR SIGNAL READOUT ENHANCEMENT IN TWO-DIMENSIONAL PAPER NETWORKS (2DPN)

CROSS-REFERENCE TO RELATED APPLICATIONS

This present U.S. patent application is a Continuation of U.S. patent application Ser. No. 15/875,016, filed on Jan. 19, 2018, which is related to and claims the priority benefit of U.S. Provisional Patent Application Ser. No. 62/447,938, filed Jan. 19, 2017, the contents of which are hereby incorporated by reference in their entirety into this disclosure.

TECHNICAL FIELD

This invention discloses an improved version of two-dimensional paper-based analytical device and method for chromatographic chemical or immunoassays. Particularly, this present invention relates to a device and a method for reducing smears and improving sharpness and intensity of test sample readout of a multi-step chemical assay or immunoassay for point-of-care diagnosis, by introducing two additional elements, a time-delay pad (2) and a mixer (1), to the conventional two-dimensional paper network device.

BACKGROUND

This section introduces aspects that may help facilitate a better understanding of the disclosure. Accordingly, these statements are to be read in this light and are not to be understood as admissions about what is or is not prior art.

Point-of-care (POC) testing has the potential to effect a paradigm shift from curative to predictive, personalized and preemptive medicine. While POC testing promotes a shift away from traditional diagnostic tests in the clinical laboratory setting to near-patient settings, providing physicians with timely diagnostic information, patients have become empowered by the ease of use of POC devices as they may personally monitor their own health quantitatively at home (F. A. Gomez, *Bioanalysis* 2013, 5, 1-3).

Paper-based analytical devices (PADs) have received considerable attention for point-of-care applications owing to the advantages of low cost, light weight, ease of handling, and fluid transport by capillary wicking (K. N. Han, et al., *Scientific Reports* 2016, 6:25710; X. Wei, et al., Anal. Chem. 2015, 87, 4275-4282). In particular, a lateral flow assay (LFA) or lateral flow test based on PADs is performed over a strip, different parts of which are assembled on a plastic backing. These components include a sample application pad, conjugate pad, nitrocellulose membrane and adsorption pad. The nitrocellulose membrane contains both test and control lines. Pre-immobilized reagents at different parts of the strip are rehydrated and become active upon flow of liquid sample. LFA combines unique advantages of biorecognition probes and chromatography. Drawbacks associated with the conventional clinical technique, enzyme linked immunosorbent assay (ELISA), were transcended by LFA. Rapidity, one step analysis, low operational cost, simple instrumentation, user friendly format, minimized or eliminated interference due to chromatographic separation, high specificity, better sensitivity, long term stability under diverse environmental conditions, and portability of the device are some unique advantages related to LFA strips (M. Sajid, et al., *J. Saudi Chemical Soc.* 2015, 19, 689-705; E. Fu, et al., *Anal. Chem.* 2012, 84(10), 4574-4579).

However, LFAs are often limited to a single chemical delivery step and not capable of the multi-step processing characteristic of high performance laboratory-based assays. To address this limitation, Fu and co-workers have developed a paper network platform that extends the conventional lateral flow test to two dimensions. The new paper-based device, named two-dimensional paper network (2DPN), allows incorporation of multi-step chemical processing, while still retaining the advantages of conventional lateral flow tests (E. Fu, et al., *Anal Chem.* 2012, 84(10): 4574-4579; P. Yager, et al., U.S. Pat. No. 9,528,987). The card platform contains reagents stored in dry form such that the user need only add sample and water. The multiple channels of reagent flow in the device are activated in a single user step of folding the card closed. The configuration of the paper network automatically delivers the appropriate volumes of i) sample plus antibody conjugated to a gold particle label, ii) a rinse buffer, and iii) a signal amplification reagent to the capture region.

Another related paper-based analytical device technology is termed loop-mediated isothermal amplification (LAMP), a method of amplifying nucleic acids at a single temperature (approximately 65° C.). LAMP uses 6 primers complimentary to 8 regions of a nucleic acid to direct thermostable polymerase to specifically amplify this region only. These primers can be labelled with fluorescein (FITC) and biotin in order to detect the amplified product via lateral flow assay or 2DPN.

Another related paper-based analytical device technology is termed enzyme-free amplification where the detection and quantification of nucleic acid sequences can be completed without enzymes or PCR. These methods include Hairpin Chain Reactions (HCR), Template Assisted Rabid Assay (TARA), branched DNA assays that can occur without additional heating or enzymes. By incorporating labelled probes such as FITC and biotin, these enzyme-free methods can be used to detect nucleic acids on LFAs and 2DPNs.

Currently available paper-based analytical devices, including published two-dimensional paper networks (2DPN), have inadequate control over the timing and delivery of multiple reagents and therefore have limited detection capabilities. These devices also have limitations in terms of sensitivity and manipulation of fluid flow. There are unmet needs for further improvement in PADs.

BRIEF SUMMARY OF INVENTIONS

This invention discloses an improved version of paper-based analytical device and a method for chromatographic chemical assay or immunoassay. Particularly, this present invention relates to a device and a method for reducing smears and improving sharpness and intensity of test sample readout using a multi-step chemical assay or immunoassay by introducing two additional elements, a time-delay pad (2) and a mixer (1), to the conventional two-dimensional paper network device.

In some aspects, this invention relates to a device for a chemical assay or an immunoassay, wherein improvement of said device over the conventional two-dimensional paper network device comprises a time delay pad (2) operably positioned right before where a previous reagent merges into its following reagent on the reagent flow path (7).

In some other aspects, this invention relates to a device for a chemical assay or an immunoassay, wherein improvement of said device over the conventional two-dimensional paper network device comprises a time delay pad (2) operably positioned right before where a previous reagent merges into its following reagent on the reagent flow path (7), and a mixer (1) operably positioned at the confluence of two or more reagent flow paths.

In some other aspects, this invention relates to a device for a chemical assay or an immunoassay as disclosed herein, wherein said mixer (1) comprises a U-shaped, a curve, a zig-zag, a square-wave, or a serpentine component wherein sufficient mixing and interactions of testing reagents with a testing sample are achieved.

In some aspects, this invention relates to a device for a chemical assay or an immunoassay as disclosed herein, wherein said mixer (1) is operably positioned on the flow path between a test sample readout (9) and a sample pad (3).

In some other aspects, this invention relates to a method for reducing smears and improving sharpness and intensity of test readout of a chemical assay or immunoassay, the method comprises providing a time delay pad (2) operably positioned before where a later reagent pad (5) merges into a previous reagent pad (4) on the reagent flow path (7), to the conventional paper-based analytical device.

In some other aspects, this invention relates to a method for reducing smears and improving sharpness and intensity of test readout of a chemical assay or immunoassay, the method may further comprise providing a mixer (1) operably positioned before the region for test sample readout (9) to the conventional paper-based analytical device.

In some other aspects, this invention relates to a method for reducing smears and improving sharpness and intensity of test readout of a chemical assay or immunoassay, the method may further comprise providing a mixer (1) operably positioned before the region for test sample readout (9) to the conventional paper-based analytical device, wherein said mixer (1) comprises a U-shaped, a curve, a zig-zag, a square-wave, or a serpentine component wherein sufficient mixing and interactions of testing reagents with a testing sample are achieved.

In some other aspects, this invention relates to a method for reducing smears and improving sharpness and intensity of test readout of a chemical assay or immunoassay, the method comprises providing a mixer (1) operably positioned before the test sample readout to the conventional paper-based analytical device, wherein said mixer comprises a U-shaped, a curve, a zig-zag, a square-wave, or a serpentine component wherein sufficient mixing and interactions of testing reagents with a testing sample are achieved.

In some aspects, this invention relates to a method for reducing smears and improving sharpness and intensity of test readout of a chemical assay or immunoassay, the method may further comprise providing a mixer (1) operably positioned before the region for test sample readout (9) to the conventional paper-based analytical device, and providing a time delay pad (2) operably positioned before where the later reagent (pad 5) merges into a previous reagent (pad 4) on the reagent flow path (7), to the conventional paper-based analytical device.

In some other aspects, this invention relates to a kit for a point-of-care a chemical assay or an immunoassay comprising
  a) a chromatographic membrane having a test line containing an immobilized analyte-binding mechanism;
  b) a plurality of reagent pads (3, 4, 5) and a sample pad (3) operably linked to said chromatographic membrane for reagents and testing sample attached to a card;
  c) a time delay pad (2), wherein said time delay pad is operably positioned right before where the later reagent (pad 5) merges into a previous reagent (pad 4) on the reagent flow path (7), upstream of the region for test readouts to the conventional paper-based analytical device
  d) a plurality of testing reagents;
  e) a wicking pad (6) and
  f) a test card that holds components of a), b), c), d) and e).

In some other aspects, this invention relates to a kit for a point-of-care a chemical assay or an immunoassay as disclosed herein, wherein the testing reagents comprise:
  1) a first reagent for sample binding and signal amplification;
  2) a second reagent of a washing solution; and
  3) a third reagent of an enzymatic substrate or additional signal amplification.

In some other aspects, this invention relates to a kit for a point-of-care a chemical assay or an immunoassay as disclosed herein, wherein said first reagent for sample binding and signal amplification are selected from the group consisting of silver nanoparticles, gold nanoparticles, polystyrene microbeads, and latex microbeads, with or without a detection analyte attached.

In some aspects, this invention relates to a kit for a point-of-care a chemical assay or an immunoassay as disclosed herein, wherein said first reagent for sample binding and signal amplification are selected from the group consisting of silver nanoparticles, gold nanoparticles, polystyrene microbeads, and latex microbeads, which is combined with a detection analyte selected from the group consisting of streptavidin, antibody, antigen, or a nucleic acid sequence, and an enzyme.

In some aspects, this invention relates to a kit for a point-of-care a chemical assay or an immunoassay as disclosed herein, wherein said first reagent for sample binding and signal amplification are selected from the group consisting of silver nanoparticles, gold nanoparticles, polystyrene microbeads, and latex microbeads, which is combined with an enzyme selected from the group consisting of horseradish peroxidase, alkaline phosphatase, glucose oxidase, and beta-galactosidase.

In some aspects, this invention relates to a kit for a point-of-care a chemical assay or an immunoassay as disclosed herein, wherein said first reagent for sample binding and signal amplification is solid or lyophilized, and rehydrated upon use.

In some aspects, this invention relates to a kit for a point-of-care a chemical assay or an immunoassay as disclosed herein, wherein said first reagent for sample binding and signal amplification is supplied as separate wet reagents.

In some aspects, this invention relates to a kit for a point-of-care a chemical assay or an immunoassay as disclosed herein, wherein said third reagent of an enzymatic substrate for horseradish peroxidase (HRP)-based detection is selected from the group consisting of 3,3',5,5'-tetramethylbenzidine, o-phenylenediamine dihydrochloride, 3,3'-diaminobenzidine, 2,2'-Azinobis [3-ethylbenzothiazoline-6-sulfonic acid], and 4-chloro-1-naphthol.

In some aspects, this invention relates to a kit for a point-of-care a chemical assay or an immunoassay as disclosed herein, wherein said third reagent for additional signal amplification comprises a silver salt, an initiator, or a fixer.

In some aspects, this invention relates to a kit for a point-of-care a chemical assay or an immunoassay as disclosed herein, wherein said chromatographic membrane is nitrocellulose.

In some aspects, this invention relates to a kit for a point-of-care a chemical assay or an immunoassay as disclosed herein, wherein said chromatographic membrane is nitrocellulose treated with a blocking reagent.

In some aspects, this invention relates to a kit for a point-of-care a chemical assay or an immunoassay as disclosed herein, wherein said chromatographic membrane is nitrocellulose treated with a blocking reagent comprising serum albumin, polyvinyl pyrrolidone, polysorbates, and sugar.

In some preferred aspects, this invention relates to a kit for a point-of-care a chemical assay or an immunoassay as disclosed herein, wherein said chromatographic membrane is nitrocellulose treated with a blocking reagent comprising bovine serum albumin, sucrose, polyvinyl pyrrolidone, and Tween 20 in phosphate buffered saline.

In some aspects, this invention relates to a kit for a point-of-care a chemical assay or an immunoassay as disclosed herein, wherein said blocking reagent comprises serum albumin, polyvinyl pyrrolidone, polysorbates, and sugar.

In some aspects, this invention relates to a kit for a point-of-care a chemical assay or an immunoassay as disclosed herein, wherein said reagent pads are an absorbent material selected from the group consisting of glass fiber, bound glass fiber, cellulose, and derivatives thereof.

In some aspects, this invention relates to a kit for a point-of-care a chemical assay or an immunoassay as disclosed herein, wherein said reagent pads of an absorbent material are treated with a blocking reagent comprising serum albumin, polyvinyl pyrrolidone, polysorbates, and sugar.

In some aspects, this invention relates to a kit for a point-of-care a chemical assay or an immunoassay as disclosed herein, wherein said blocking reagent comprises serum albumin.

In some aspects, this invention relates to a kit for a point-of-care a chemical assay or an immunoassay as disclosed herein, wherein said blocking reagent comprises a sugar.

In some aspects, this invention relates to a kit for a point-of-care a chemical assay or an immunoassay as disclosed herein, wherein said blocking reagent comprises polyvinyl pyrrolidone.

In some aspects, this invention relates to a kit for a point-of-care a chemical assay or an immunoassay as disclosed herein, wherein said blocking reagent comprises a polysorbate.

In some aspects, this invention relates to a kit for a point-of-care a chemical assay or an immunoassay as disclosed herein, wherein said blocking reagent comprises Tween 20.

In some aspects, this invention relates to a kit for a point-of-care a chemical assay or an immunoassay as disclosed herein, wherein said blocking reagent comprises sucrose.

In some aspects, this invention relates to a kit for a point-of-care a chemical assay or an immunoassay as disclosed herein, wherein said test card is folded over to bring the reagent pads into contact with the chromatographic materials to activate simultaneous flow of reagents.

In some aspects, this invention relates to a kit for a point-of-care a chemical assay or an immunoassay as disclosed herein, wherein the kit further comprises a non-adhesive film positioned between the folded reagent pads and said chromatographic membrane and is then removed in order to activate simultaneous flow of reagents.

In some other aspects, this invention relates to a kit for a point-of-care a chemical assay or an immunoassay as disclosed herein, wherein said test card has one or more access holes through which liquid reagents are added to the reagent pads upon folding and a non-adhesive film that is removed in order to activate simultaneous flow of reagents In some other illustrative embodiments, this invention relates to a kit for a point-of-care a chemical assay or an immunoassay as disclosed herein, wherein said enzymatic amplification affording signal enhancement and amplification comprises a visible, a fluorescent, a chemiluminescent, a magnetic, a thermal, or an electrochemical signal.

BRIEF DESCRIPTION OF THE DRAWINGS

Embodiments of the present disclosure will now be described by way of example in greater detail with reference to the attached figures.

DETAILED DESCRIPTION

Figure 1A:
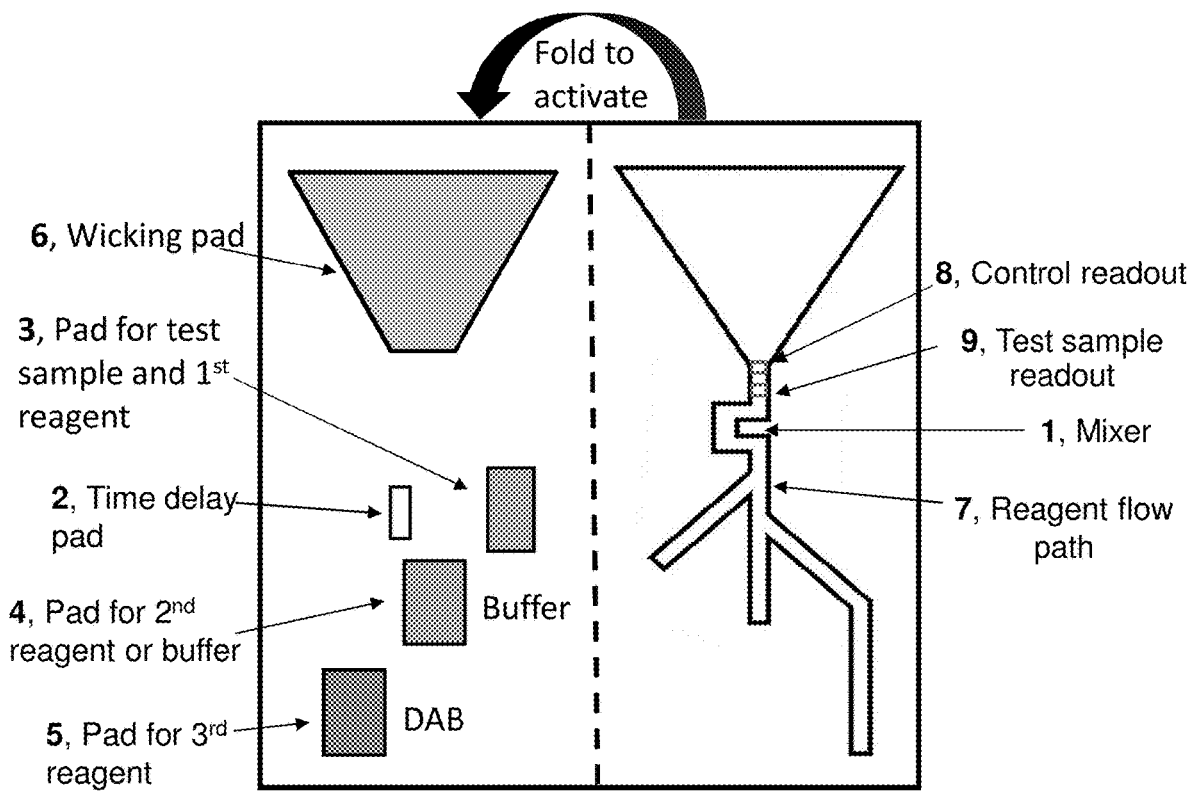
FIG. 1A shows the open view of a card with the essential elements of the two-dimensional paper network (2DPN) device on the added two elements (1, mixer and 2, time delay pad) to the conventional 2DPN device and the nitrocellulose template shape. An additional element (10), not shown on the drawing, is a non-adhesive film covering each side of the card, which separates the contents of the two sides from mixing during storage and transportation.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

This invention discloses a paper-based analytical device and method for chromatographic chemical or immunoassays. Particularly, this present invention relates to a device and a method for reducing smears and improving sharpness and intensity of test sample readout of a multi-step chemical assay or immunoassay for point-of-care diagnosis, by introducing two additional elements, a time-delay pad (2) and a mixer (1), to the conventional two-dimensional paper network device.

In some illustrative embodiments, this invention relates to a device for a chemical assay or an immunoassay, wherein improvement of said device over the conventional two-dimensional paper network device comprises a time delay pad (2) operably positioned right before where a previous reagent merges into its following reagent on the reagent flow path (7).

In some other illustrative embodiments, this invention relates to a device for a chemical assay or an immunoassay, wherein improvement of said device over the conventional two-dimensional paper network device comprises a time delay pad (2) operably positioned right before where a previous reagent merges into its following reagent on the reagent flow path (7), and a mixer (1) operably positioned at the confluence of two or more reagent flow paths.

In some other illustrative embodiments, this invention relates to a device for a chemical assay or an immunoassay as disclosed herein, wherein said mixer (1) comprises a U-shaped, a curve, a zig-zag, a square-wave, or a serpentine component wherein sufficient mixing and interactions of testing reagents with a testing sample are achieved.

In some other illustrative embodiments, this invention relates to a device for a chemical assay or an immunoassay as disclosed herein, wherein said mixer (1) is operably positioned on the flow path between a test sample readout and a sample pad (3).

In some other illustrative embodiments, this invention relates to a method for reducing smears and improving sharpness and intensity of test readout of a chemical assay or immunoassay, the method comprises providing a time delay pad (2) operably positioned before where a later reagent pad (5) merges into a previous reagent pad (4) on the reagent flow path (7), to the conventional paper-based analytical device.

In some other illustrative embodiments, this invention relates to a method for reducing smears and improving sharpness and intensity of test readout of a chemical assay or immunoassay, the method may further comprise providing a mixer (1) operably positioned before the region for test sample readout (9) to the conventional paper-based analytical device.

In some other illustrative embodiments, this invention relates to a method for reducing smears and improving sharpness and intensity of test readout of a chemical assay or immunoassay, the method may further comprise providing a mixer (1) operably positioned before the region for test sample readout (9) to the conventional paper-based analytical device, wherein said mixer (1) comprises a U-shaped, a curve, a zig-zag, a square-wave, or a serpentine component wherein sufficient mixing and interactions of testing reagents with a testing sample are achieved.

In some other illustrative embodiments, this invention relates to a method for reducing smears and improving sharpness and intensity of test readout of a chemical assay or immunoassay, the method comprises providing a mixer (1) operably positioned before the test sample readout to the conventional paper-based analytical device, wherein said mixer comprises a U-shaped, a curve, a zig-zag, a square-wave, or a serpentine component wherein sufficient mixing and interactions of testing reagents with a testing sample are achieved.

In some other illustrative embodiments, this invention relates to a method for reducing smears and improving sharpness and intensity of test readout of a chemical assay or immunoassay, the method may further comprise providing a mixer (1) operably positioned before the region for test sample readout (9) to the conventional paper-based analytical device, and providing a time delay pad (2) operably positioned before where the later reagent (pad 5) merges into a previous reagent (pad 4) on the reagent flow path (7), to the conventional paper-based analytical device.

In some other illustrative embodiments, this invention relates to a kit for a point-of-care a chemical assay or an immunoassay comprising
a) a chromatographic membrane having a test line containing an immobilized analyte-binding mechanism;
b) a plurality of reagent pads (3, 4, 5) and a sample pad (3) operably linked to said chromatographic membrane for reagents and testing sample attached to a card;
c) a time delay pad (2), wherein said time delay pad is operably positioned right before where the later reagent (pad 5) merges into a previous reagent (pad 4) on the reagent flow path (7), upstream of the region for test readouts to the conventional paper-based analytical device
d) a plurality of testing reagents;
e) a wicking pad (6) and
f) a test card that holds components of a), b), c), d) and e).

In some other illustrative embodiments, this invention relates to a kit for a point-of-care a chemical assay or an immunoassay as disclosed herein, wherein the testing reagents comprise:
1) a first testing reagent for sample binding and signal amplification;
2) a second testing reagent of a washing solution; and
3) a third testing reagent of an enzymatic substrate or additional signal amplification.

In some other illustrative embodiments, this invention relates to a kit for a point-of-care a chemical assay or an immunoassay as disclosed herein, wherein said first reagent for sample binding and signal amplification are selected from the group consisting of silver nanoparticles, gold nanoparticles, polystyrene microbeads, and latex microbeads, with or without a detection analyte attached.

In some other illustrative embodiments, this invention relates to a kit for a point-of-care a chemical assay or an immunoassay as disclosed herein, wherein said first reagent for sample binding and signal amplification are selected from the group consisting of silver nanoparticles, gold nanoparticles, polystyrene microbeads, and latex microbeads, which is combined with a detection analyte selected from the group consisting of streptavidin, antibody, antigen, or a nucleic acid sequence, and an enzyme.

In some other illustrative embodiments, this invention relates to a kit for a point-of-care a chemical assay or an immunoassay as disclosed herein, wherein said first reagent for sample binding and signal amplification are selected from the group consisting of silver nanoparticles, gold nanoparticles, polystyrene microbeads, and latex microbeads, which is combined with an enzyme selected from the group consisting of horseradish peroxidase, alkaline phosphatase, glucose oxidase, and beta-galactosidase.

In some other illustrative embodiments, this invention relates to a kit for a point-of-care a chemical assay or an immunoassay as disclosed herein, wherein said first reagent for sample binding and signal amplification is solid or lyophilized, and rehydrated upon use.

In some other illustrative embodiments, this invention relates to a kit for a point-of-care a chemical assay or an immunoassay as disclosed herein, wherein said first reagent for sample binding and signal amplification is supplied as separate wet reagents.

In some other illustrative embodiments, this invention relates to a kit for a point-of-care a chemical assay or an immunoassay as disclosed herein, wherein said third reagent of an enzymatic substrate for horseradish peroxidase-based detection is selected from the group consisting of 3,3',5,5'-tetramethylbenzidine, o-phenylenediamine dihydrochloride, 3,3'-diaminobenzidine, 2,2'-Azinobis [3-ethylbenzothiazoline-6-sulfonic acid], and 4-chloro-1-naphthol.

In some other illustrative embodiments, this invention relates to a kit for a point-of-care a chemical assay or an immunoassay as disclosed herein, wherein said third reagent for additional signal amplification comprises a silver salt, an initiator, or a fixer.

In some other illustrative embodiments, this invention relates to a kit for a point-of-care a chemical assay or an immunoassay as disclosed herein, wherein said chromatographic membrane is nitrocellulose.

In some other illustrative embodiments, this invention relates to a kit for a point-of-care a chemical assay or an immunoassay as disclosed herein, wherein said chromatographic membrane is nitrocellulose treated with a blocking reagent.

In some preferred embodiments, this invention relates to a kit for a point-of-care a chemical assay or an immunoassay as disclosed herein, wherein said chromatographic membrane is nitrocellulose treated with a blocking reagent comprising serum albumin, polyvinyl pyrrolidone, polysorbates, and sugar.

In some other illustrative embodiments, this invention relates to a kit for a point-of-care a chemical assay or an immunoassay as disclosed herein, wherein said blocking reagent comprises serum albumin, polyvinyl pyrrolidone, polysorbates, and sugar.

In some other illustrative embodiments, this invention relates to a kit for a point-of-care a chemical assay or an immunoassay as disclosed herein, wherein said reagent pads are an absorbent material selected from the group consisting of glass fiber, bound glass fiber, cellulose, and derivatives thereof.

In some other illustrative embodiments, this invention relates to a kit for a point-of-care a chemical assay or an immunoassay as disclosed herein, wherein said reagent pads of an absorbent material are treated with a blocking reagent.

In some other illustrative embodiments, this invention relates to a kit for a point-of-care a chemical assay or an immunoassay as disclosed herein, wherein said reagent pads of an absorbent material are treated with a blocking reagent comprising serum albumin, polyvinyl pyrrolidone, polysorbates, and sugar.

In some other illustrative embodiments, this invention relates to a kit for a point-of-care a chemical assay or an immunoassay as disclosed herein, wherein said blocking reagent comprises serum albumin.

In some other illustrative embodiments, this invention relates to a kit for a point-of-care a chemical assay or an immunoassay as disclosed herein, wherein said blocking reagent comprises a sugar.

In some other illustrative embodiments, this invention relates to a kit for a point-of-care a chemical assay or an immunoassay as disclosed herein, wherein said blocking reagent comprises polyvinyl pyrrolidone.

In some other illustrative embodiments, this invention relates to a kit for a point-of-care a chemical assay or an immunoassay as disclosed herein, wherein said blocking reagent comprises a polysorbate.

In some other illustrative embodiments, this invention relates to a kit for a point-of-care a chemical assay or an immunoassay as disclosed herein, wherein said blocking reagent polysorbate comprises Tween 20.

In some other illustrative embodiments, this invention relates to a kit for a point-of-care a chemical assay or an immunoassay as disclosed herein, wherein said blocking reagent sugar comprises sucrose.

In some other illustrative embodiments, this invention relates to a kit for a point-of-care a chemical assay or an immunoassay as disclosed herein, wherein said test card is folded over to bring the reagent pads into contact with the chromatographic materials to activate simultaneous flow of testing reagents.

In some other illustrative embodiments, this invention relates to a kit for a point-of-care a chemical assay or an immunoassay as disclosed herein, wherein the kit further comprises a non-adhesive film (10) positioned between the folded reagent pads and said chromatographic membrane and is then removed in order to activate simultaneous flow of reagents.

In some other illustrative embodiments, this invention relates to a kit for a point-of-care a chemical assay or an immunoassay as disclosed herein, wherein said test card has one or more access holes through which liquid reagents are added to the reagent pads upon folding.

In some other illustrative embodiments, this invention relates to a kit for a point-of-care a chemical assay or an immunoassay as disclosed herein, wherein said enzymatic amplification affording signal enhancement and amplification comprises a visible, a fluorescent, chemiluminescent, magnetic, or electrochemical signal.

In the present disclosure the term "about" can allow for a degree of variability in a value or range, for example, within 20%, within 10%, within 5%, or within 1% of a stated value or of a stated limit of a range.

In the present disclosure, the term "substantially" can allow for a degree of variability in a value or range, for example, within 80%, within 90%, within 95%, or within 99% of a stated value or of a stated limit of a range.

The present technology describes various embodiments of devices for processing, analyzing, detecting, measuring, and separating components of a fluid. The devices can be used to perform these processes on a microfluidic scale, and with control over fluid and reagent transport. In one embodiment, for example, a device for performing chemical processes can include a porous wick comprising a pathway defined by an input end, an output end, and a length between the input end and the output end. The device may also find application in an enzymatic process or other affinity-based chemical and biochemical processes, which is involved in diagnosis or quality control. The pathway is configured to wick fluid from the input end to the output end by capillary action. The device can further include a reagent placed on the pathway. For example, the reagent can be placed in a pattern configured to control a spatial or temporal distribution of the reagent along the pathway upon wetting of the pathway.

As used herein, "porous element" or "porous membrane" refers to a porous membrane (e.g., a wick, pathway, leg, pad, delivery channel, etc.) through which fluid can travel by capillary action, such as paper, nitrocellulose, nylon, glass fiber, and the like. Unless the context clearly requires otherwise, a porous element can be two-dimensional or three-dimensional (when considering its height in addition to its length and width). Additionally, a porous membrane can be a single layer or may comprise two or more membranous layers. Although in some embodiments a specific term may be used (e.g., "wick," "pathway," "leg," "pad," "delivery channel," etc.), it should be understood that use of a different porous element is also within the scope of the present technology.

As used herein, "wettably distinct" means being capable of being wetted by contact with separate fluids without mixing of the fluids at the point of initial wetting. For example, two input legs are wettably distinct if they are physically separated so that each leg could be brought into contact with a separate fluid reservoir. Pathways can be made wettably distinct by a variety of means including, but not limited to, separation via distinct edges (e.g., cut as separate pathways) and separation via an impermeable barrier.

As used herein, a two-dimensional paper network ("2DPN") refers to a system that includes at least two interconnected wettably distinct wicks, pathways, and/or legs. A one-dimensional paper network ("1DPN") refers to a system that only includes a single wick, pathway, or leg. A "pseudo-1 DPN" refers to a single wick, pathway or leg directly coupled to one or more fluid sources (e.g., without a wettably distinct leg therebetween).

Point of care (POC) testing has become the most famous way of diagnosis in clinical analysis, food safety and environment. Compared to centralized labs, POC provides prompt results in shorter times. Lateral flow assay (LFA) based POC devices are among very rapidly growing strategies for qualitative and quantitative analysis. LFA is performed over a strip, different parts of which are assembled on a plastic backing. These parts are sample application pad, conjugate pad, nitrocellulose membrane and adsorption pad. Nitrocellulose membrane is further divided into test and control readout (lines). Pre-immobilized reagents at different parts of the strip become active upon flow of liquid sample (M. Sajid, et al., *J. Saudi Chemical Soc.* 2015, 19, 689-705).

Sample application pad: It is made of cellulose and/or glass fiber and sample is applied on this pad to start the assay. Its function is to transport the sample to other components of lateral flow test strip. The sample pad should be capable of transportation of the sample in a smooth, continuous and homogenous manner. Sample application pads are sometimes designed to pretreat the sample before its release. This pretreatment may include separation of sample components, removal of interferences, adjustment of pH, etc.

Conjugate pad: It is the place where labeled biorecognition molecules are dispensed. The material of the conjugate pad should immediately release labeled conjugates upon contact with a moving liquid sample. The labeled conjugate should remain stable and retain its chemical activity over the entire life span of the lateral flow strip. Any variations in dispensing, drying or release of the conjugate can change the results of the assay significantly. Poor preparation of the labeled conjugate can adversely affect the sensitivity of the assay. Glass fiber, cellulose, polyesters and some other materials are used to make conjugate pads for LFA. The nature of the conjugate pad material has an effect on the release of the labeled conjugate and the sensitivity of the assay.

Nitrocellulose membrane: Selecting the correct nitrocellulose membrane is highly critical in determining the sensitivity of the LFA. Nitrocellulose membranes are available in different grades. Test and control lines are applied onto this piece of membrane. An ideal membrane should provide support and good binding to capture probes (antibodies, aptamers etc.). Nonspecific adsorption over test and control lines may affect the results of the assay significantly, thus a good membrane is characterized by lesser non-specific adsorption in the regions of test and control lines. The wicking rate of the nitrocellulose membrane can influence assay sensitivity. These membranes are easy to use, inexpensive, and offer high affinity for proteins and other biomolecules. Proper dispensing of bioreagents, drying, and blocking play a role in improving the sensitivity of the assay.

Adsorbent pad: It works as sink to wick away liquid at the end of the strip. It also helps in maintaining flow rate of the liquid over the membrane, and stops back flow of the sample. Adsorbent capacity to hold liquid can play an important role in the results of the assay. All these components are fixed or mounted over a backing card. Materials for the backing card are highly flexible because they do not affect the reagent reactions or flow within the LFA, except in providing a platform for proper assembling of all the components. Thus, the backing card serves as a support and it makes easy to handle the strip.

Major steps in LFA include (i) preparation of antibody specific to the target analyte (ii) preparation of label (iii) labeling of biorecognition molecules (iv) assembling of all components onto a backing card before dispensing of reagents at their proper pads (v) application of sample and obtaining results (M. Sajid, et al., 2015).

A prototype, chromatographic immunoassay device for lateral flow assay disclosed herein is based on a disruptive platform technology called the Template Assisted Rapid Assay (TARA), which works directly on diverse biological samples without nucleic acid purification. A microfluidic-based automated 2DPN TARA card can be applied broadly to applications for point-of-care or in-the-field nucleic acid detection of infectious agents or bio-threats (e.g., radiation dose estimation using gene expression detection). TARA uses a target template-dependent chemical transfer reaction to amplify the nucleic acid target sequences and uses gold nanoparticle/horseradish peroxidase for signal amplification and detection on a microfluidic-based 2DPN TARA card, which seamlessly integrates minimal sample preparation with target amplification and detection (See FIGS. 2A, 2B, 3, 4A and 4B). The test eliminates the need for an expensive doctors' office visit, excess devices for sample collection, resource-intensive refrigerated storage and transport of samples, and access to instrumentation and laboratory tests.

The present invention may be better understood in light of the following non-limiting, illustrative examples.

Paper Component Preparation (for the Device Shown in FIGS. 1 and 2B):

1. Apply about 1 µL each of anti-FITC test line and biotinylated goat secondary antibody control line to the cut nitrocellulose membrane in the region indicated by FIG. 1.
2. Dry the nitrocellulose membrane in an oven, under conditions such as 10 minutes at 65-80° C. to dry the test and control lines onto the material.
3. Saturate the entire nitrocellulose membrane with at least 20 µL of blocking solution. Oversaturation is recommended.
4. Place the device back into the oven for the same conditions as in step 3, until the entire membrane is completely dry again.

Blocking Reagent Solution Recipe: Phosphate buffered saline (PBS) containing 5% sucrose, 2% bovine serum albumin (BSA), 0.25% polyvinyl pyrrolidine (PVP), and 0.05% Tween 20.

Reagent Preparation (for the device shown in FIGS. 1 and 2B): The following nomenclature is used for the reagents. These numbers correspond to the reagent numbers in FIG. 1A.

TABLE 1

Figure 1B:
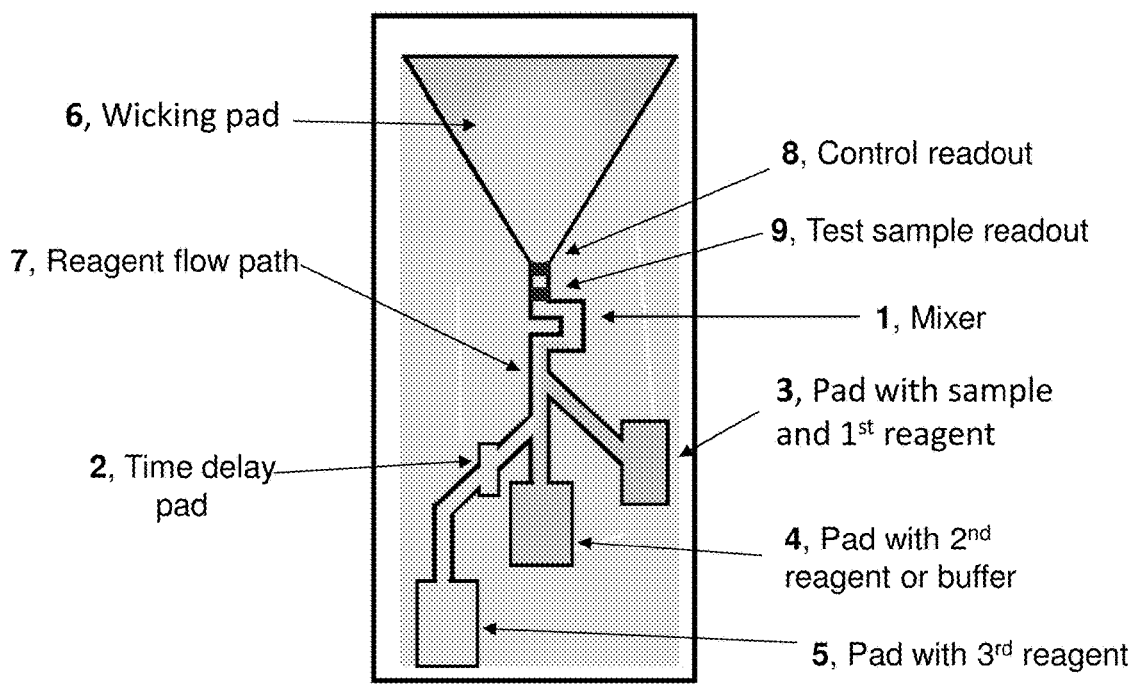
FIG. 1B shows the closed view when the card is fold over to activate and start the assay process. Before folding the two sides of the card to start the assay process, element 10 (the non-adhesive covering film) is first removed.
Figure 2A:
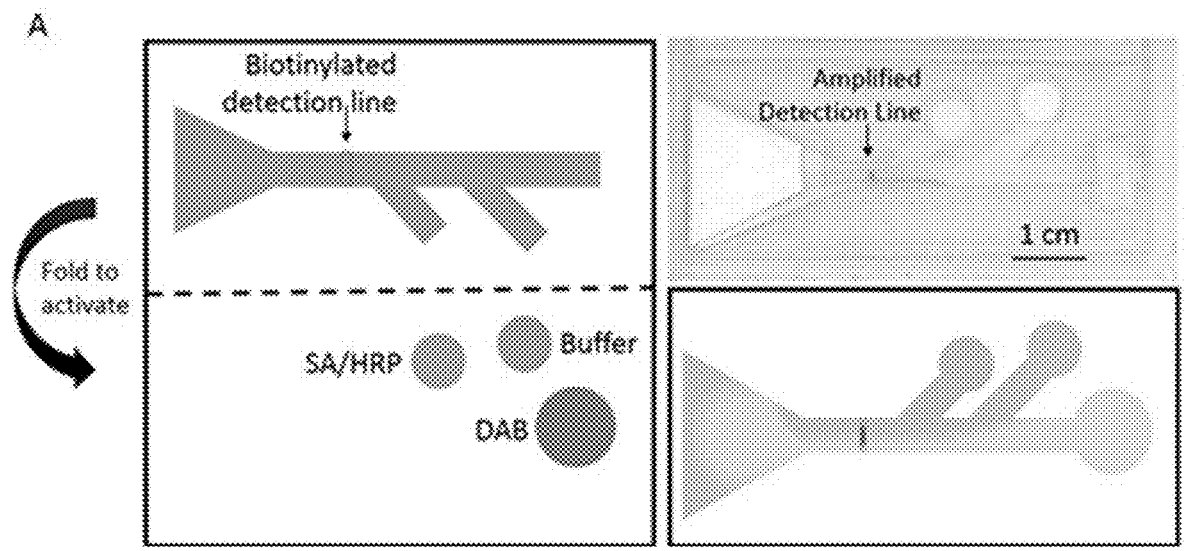
FIG. 2A shows the first generation 2DPN cards and the testing result. Initially, reagents are added to the reagent pads; the card is then folded to initiate reagent flow, and reagents are delivered sequentially to the detection zone. An image of a first generation 2DPN card shows signal amplification at the control line.
Figure 2B:
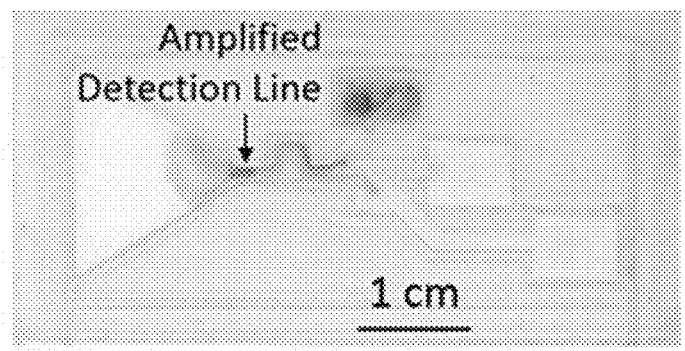
FIG. 2B shows the improved fluidic controls in the second generation 2DPN disclosed herein, with the addition of the mixing element and the time delay valve. The second generation 2DPN device shows improved signal amplification at the control line.
Figure 2B:
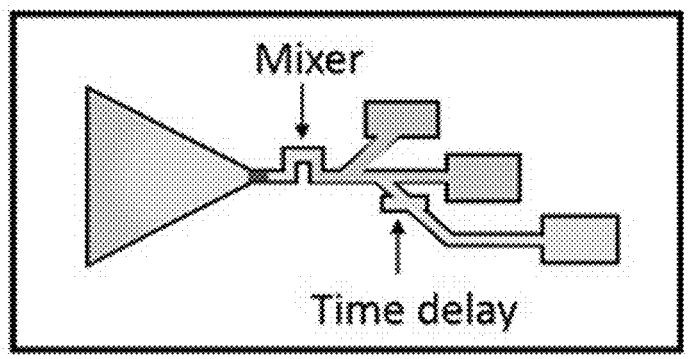

Summary of Reagent Preparation and Uses (for the device shown in FIG. 1 and 2B)

| Reagent No. | Amount (µL) | Preparation | Special notes |
| --- | --- | --- | --- |
| #1 Streptavidin HRP conjugated GNPs | 15 | Dilute the supernatant with blocking solution to a 1:1 volumetric ratio. | Inspect color when choosing test tube. Dark red is considered well prepared. Blue or purple colors are not ideal. Do not sonicate or agitate the test tube; use only the supernatant and not any precipitated materials. |
| #2 PBST | 20 | | phosphate buffered saline with 0.05% Tween 20 |
| #3 DAB (3,3'-diaminobenzidine tetrahydrochloride) | 20 | DAB is made by mixing DAB + (peroxide) chromogen and DAB + substrate. Ratio can be found in kit instructions. 29.4 µL DAB + sub. and 59 µL DAB + chr. These reagents are carcinogens. Dispose of tips in a biohazard bag, and change gloves after handling reagents. | DAB is time sensitive; mixing will eventually cause the reaction to proceed. Prepare this reagent no more than 10 minutes before actually running the test. |

2DPN Test Preparation, Running, and Data Collection (for the Device Shown in FIGS. 1 and 2B):

This section contains illustrative steps needed to run, collect, and analyze the data from the 2DPN test.

I. Scanner Set Up
1. Start EPSON Scan software and turn on the scanner
2. Orient the device in the same way each time for visualization and consistency
3. Use the preview function to zoom into the desired area, and scan to set the file name and desired folder II. Adding Reagents
1. Apply the reagents to the pad. Refer to Table 1 and FIG. 1A for the amounts and locations of these reagents.
2. Use a micropipette to carefully drop the reagents onto their respective pads. Take care to place the drops onto the pad and not to spill liquid onto the plastic areas. Overflow may disrupt the test results.

III. Initiating Test
1. Once all the reagents have been applied to their respective pads, carefully fold over the nitrocellulose side, without making contact with the reagent pads.

Line up the plastic and nitrocellulose with the pads, not the borders of the device, as precisely as possible.
3. Once all components are lined up, quickly press down the nitrocellulose with a swift motion. Make sure that contact between the nitrocellulose and the pads is made at the same instant, so all reagents begin flowing at the exact same time.
4. Immediately following, place the device on the table and use a pen or similar tool to press down on the edges and spaces where both adhesive sides should contact, to increase pressure between the glass fiber pads and the nitrocellulose. Never push down on the pads at any time.
5. Begin scanning as soon as possible, making sure that the device is oriented the same way each time. Take scans in rapid sequence for 3-5 minutes to track the flow progression.
6. Monitor the scans to track flow progress and watch for continuous flow, adhesion, background, unusual flow patterns, etc. It is good practice to look through the scans as they are collected to visibly monitor the reaction in real time, and to observe the root of any problems that may occur.
7. Continue scanning for the next 60-90 minutes. The rate of scans may slow down after the first 10 minutes, taking scans once every five minutes.
8. During the test, the device may need re-adhesion to continue flowing. If flow slows significantly, take the device out of the scanner and re-adhere the edges and adhesive areas with a pen or similar tool. Never apply pressure to the pads directly, or the flow patterns of reagents will be severely disrupted.
9. The test is considered concluded at a minimum of 60 minutes, or when the fluid front has not moved for at least 5 minutes.

Food Coloring Test Run (for the device shown in FIGS. 1 and 2B): This section describes the food coloring test used as a model for studying the flow patterns of the reagents. It may be used to adjust nitrocellulose channel dimensions, reagent pad locations, or any other controlled variables. It is also a useful tool to test in parallel with a reagent test for comparative analysis.
 I. Preparation of Solutions and Paper Components
 1. Prepare the nitrocellulose and glass fiber pads the same way as in the Paper Component Preparation section.
 2. Use red, blue, and yellow food coloring to create 1% solutions in PBST. Refer to FIG. 1A for colored solution placement.
 II. Conjugate Nanoparticles
 1. Gold nanoparticles (GNP) of 40 nm are conjugated to Strep HRP (horseradish peroxidase) to track its binding to the biotinylated goat secondary antibody.
 2. Nanoparticle (NP) colors: As described in the documentation that comes with the kit, the nanoparticles used should be a pink/red color. Anything that turns blue or purple is an indicator that the NPs are no longer viable and should be discarded.
 3. Add 40 µL of pH buffer to Eppendorf tube
 4. Add 1 mL of gold nanoparticles directly from kit. Pipette up and down several times to mix.
 5. Add 20 µL of Streptavidin-Poly HRP (0.5 mg/mL)
 6. Incubate on rocker for 15 min. at room temp, with tubes taped down so liquid mixes back and forth along the tube
 7. Add 1 mL of 10% NaCl
 8. Incubate on rocker for 30 min.
 9. Centrifuge at 300×g for 10 minutes
 10. If a pellet is present, transfer supernatant to new tube and discard pellet. Otherwise, leave solution in Eppendorf tube.
 11. Centrifuge at 3000×g for 30 minutes
 12. Discard supernatant (should be a clear solution)
 13. Resuspend pellet in 100 µL PBS, 5% Sucrose, 2% BSA, 0.25% PVP, 0.05% Tween in PBS.

Fluidic Control in 2DPNs—Comparison Between Conventional 2DPN Device and the Improved 2DPN Device Disclosed Herein.

Conventional 2DPN as shown in FIG. 2A provides reagent transport and detection line within 35 minutes of time. However, due to low Reynolds numbers in micro- and paper fluidic devices, fluids do not mix very well in straight channels and reagent timing resulted in background "smears" of signal (top panel of FIG. 2A). We have discovered ways to further optimize the fluidics in the device, including incorporation of streptavidin-HRP conjugated gold nanoparticles (Cytodiagnostics, Ontario, CA) to ensure detection of initial flow, a U shaped mixer (1, FIGS. 1A and 1B) for even delivery of all reagents, and a time delay pad (2, FIGS. 1A and 1B) that slows the delivery of DAB chromogen until rinsing is completed while reducing the overall signal amplification reaction time to less than 10 minutes (FIG. 2B).

Figure 3:
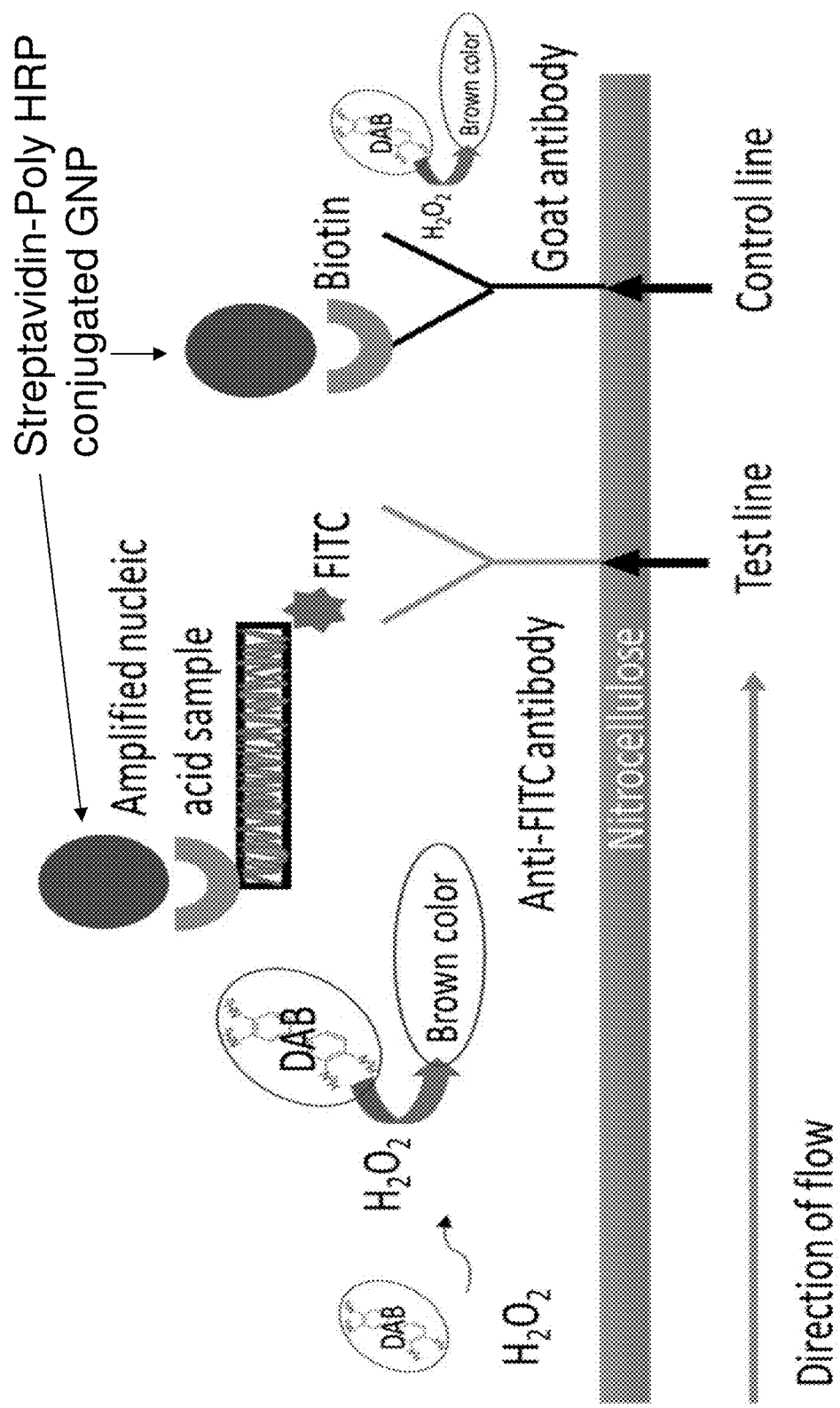
FIG. 3 shows schematic of signal amplification and detection mechanism using streptavidin-poly horseradish peroxidase (HRP) conjugated onto gold nanoparticles (GNP) as the first testing reagent, and a fluorescein (FITC) and biotin tagged nucleic acid as a sample, phosphate buffered saline as the second testing reagent, and 3,3'-diaminobenzidine (DAB) in the third testing reagent. Upon addition to the first testing reagent, the biotinylated sample binds to the streptavidin in the reagent. These flowing through the chromatographic strip and binding to the test readout (line) in the detection zone. Excess testing reagent 1 binds to the control readout (line) in the detection zone. Unbound testing reagent 1 is rinsed from the detection zone by testing reagent 2 and then the test and control readout (line) signals are further amplified for visual detection by DAB in testing reagent 3 reacting with the HRP in testing reagent 1 to form a brown precipitate located at the test and control readout (lines).
Figure 4A:
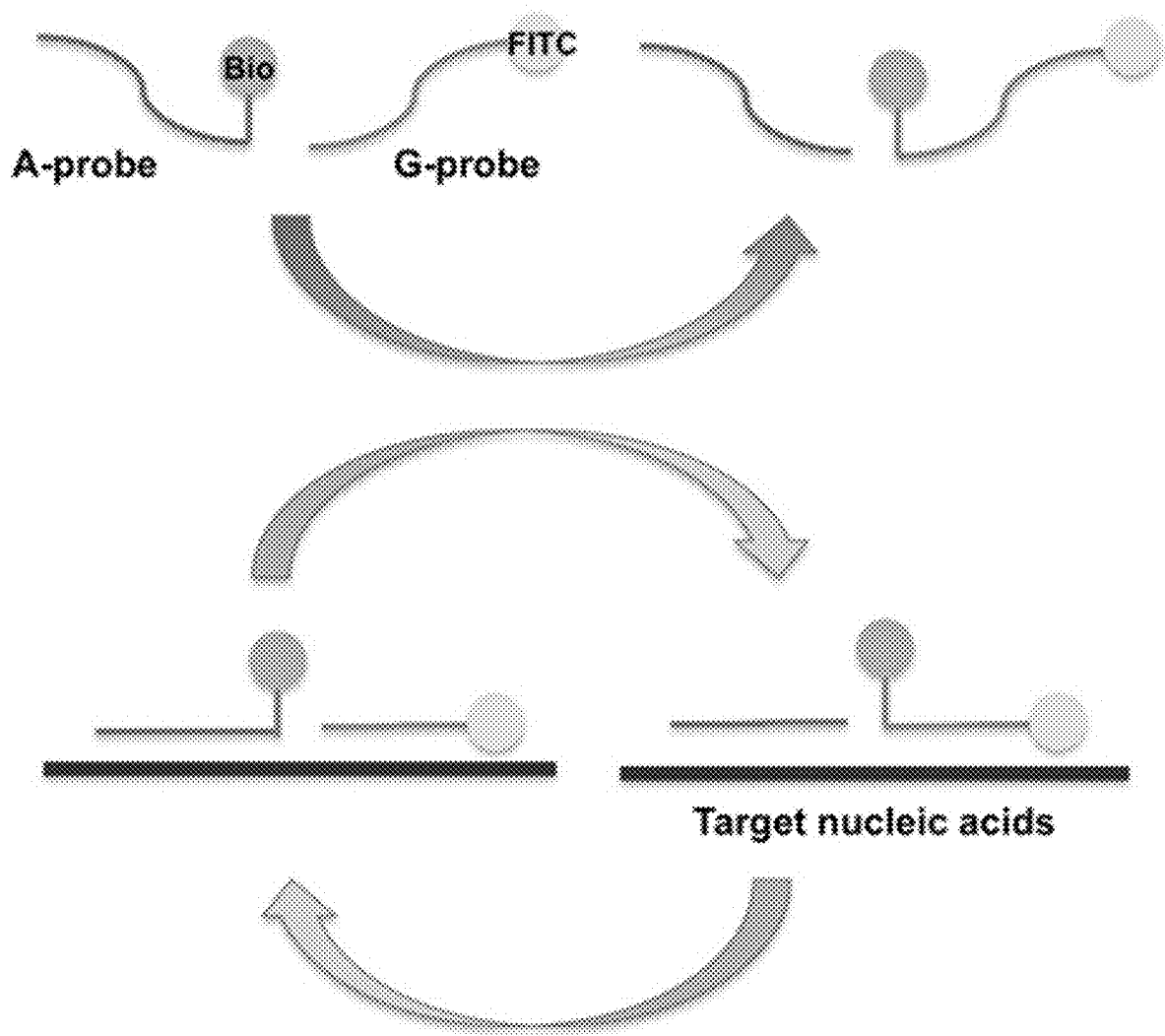
FIG. 4A describes the general principle of template assisted transfer reaction. The G-probe (N-terminus isocysteine moiety) is shown in orange; the A-probe (C-terminus thioester-link, and a biotin group) is shown in blue; and the dark blue line shows target nucleic acids.
Figure 4B:
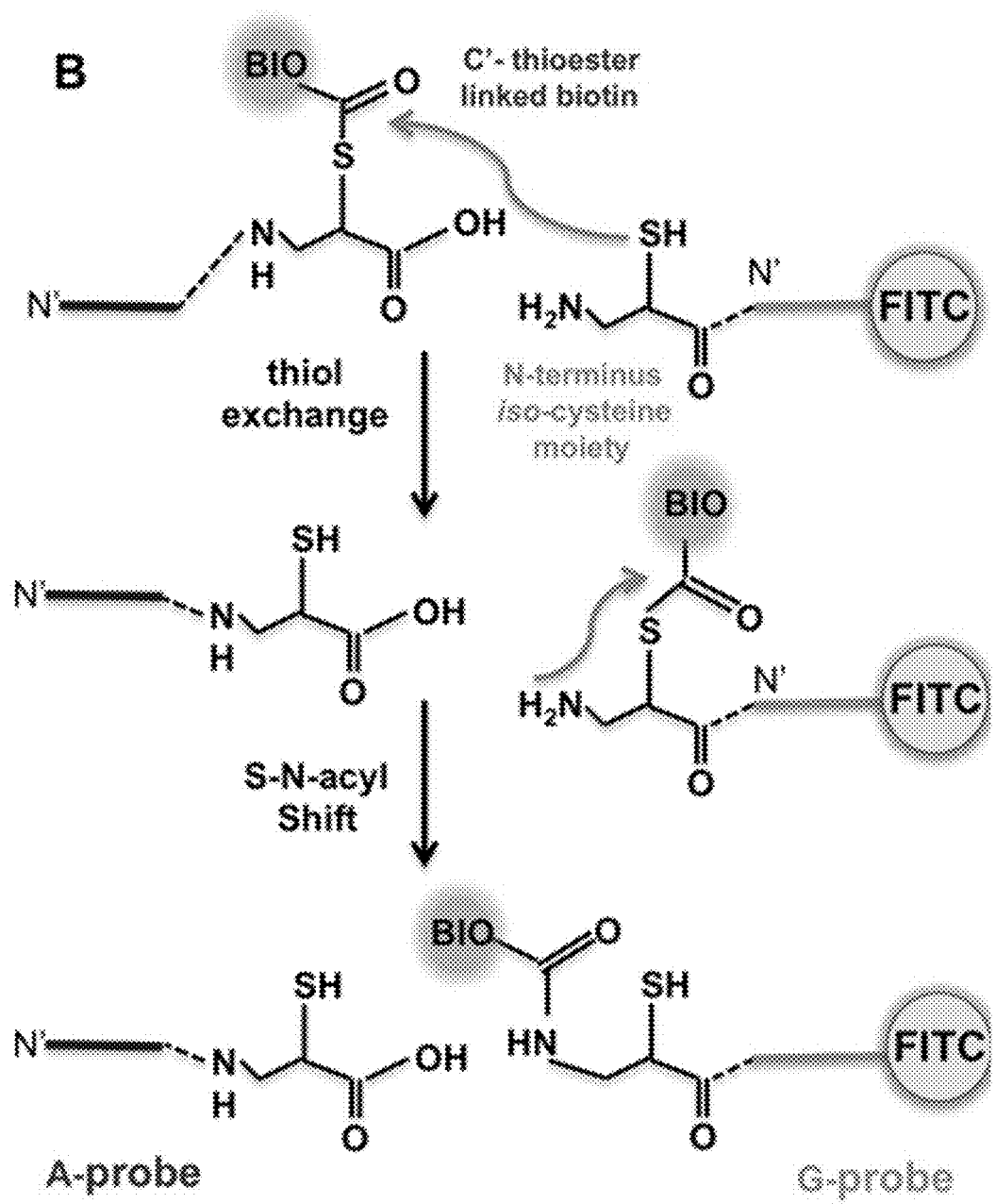
FIG. 4B shows the principle of template assisted transfer reaction involving transferring a reporter group by a native chemical ligation-like reaction. The reporter group, indicated by the blue circle (e.g. antigen, antibody or biotin) is first transferred to a thiol group of the acceptor G-probe, and then transferred in an irreversible intramolecular reaction to an amino group of the acceptor G-probe.

In paper-based devices, the use of paper fluidic networks can provide a simple method to connect reagent modules enabling multi-step reactions such as HRP mediated signal amplification of lateral flow assays (S. Ramachandran, et al., *Analyst*, 2014, 139, 1456-1462). Building off of our preliminary 2DPN HRP amplification assays, the new 2DPN device we disclosed here amplifies the TARA signal, and the end-user is required to perform only a single step before viewing the amplified detection line: add TARA amplicons and buffer to the appropriate pads on the card and fold the 2DPN to activate. The chemical and enzymatic mechanisms are shown in FIGS. 3, 4A and 4B.

FIG. 1A shows the open view of a card with the essential elements of the two-dimensional paper network (2DPN) device on the added two elements (1, mixer and 2, time delay pad) to the conventional 2DPN device and the nitrocellulose template shape. An additional element (10), not shown on the drawing, is a non-adhesive film covering each side of the card, which separates the contents of the two sides from mixing during storage and transportation. FIG. 1B shows the closed view when the card is fold over to activate and start the assay process. Before folding the two sides of the card to start the assay process, element 10 is first removed.

FIG. 2A shows the first generation 2DPN cards and the testing result. Initially, reagents are added to the reagent pads; the card is then folded to initiate reagent flow, and reagents are delivered sequentially to the detection zone. An image of a first generation 2DPN card shows signal amplification at the center of the detection zone.

FIG. 2B shows the improved fluidic controls in the second generation 2DPN disclosed herein, with the addition of the mixing element and the time delay valve. The second generation 2DPN device shows improved signal amplification across the detection zone.

FIG. 3 shows schematic of signal amplification and detecting mechanism using streptavidin-poly horseradish peroxidase (HRP) conjugated gold nanoparticle (GNP).

FIG. 4A describes the general principle of template assisted transfer reaction. The G-probe (N-terminus isocysteine moiety) is shown in orange; the A-probe (C-terminus thioester-link, and a biotin group) is shown in blue; and the dark blue line shows target nucleic acids.

FIG. 4B shows the principle of template assisted transfer reaction involving transferring a reporter group by a native chemical ligation-like reaction. The reporter group, indicated by the blue circle (e.g. antigen, antibody or biotin) is first transferred to a thiol group of the acceptor G-probe, and then transferred in an irreversible intramolecular reaction to an amino group of the acceptor G-probe.

Figure 5:
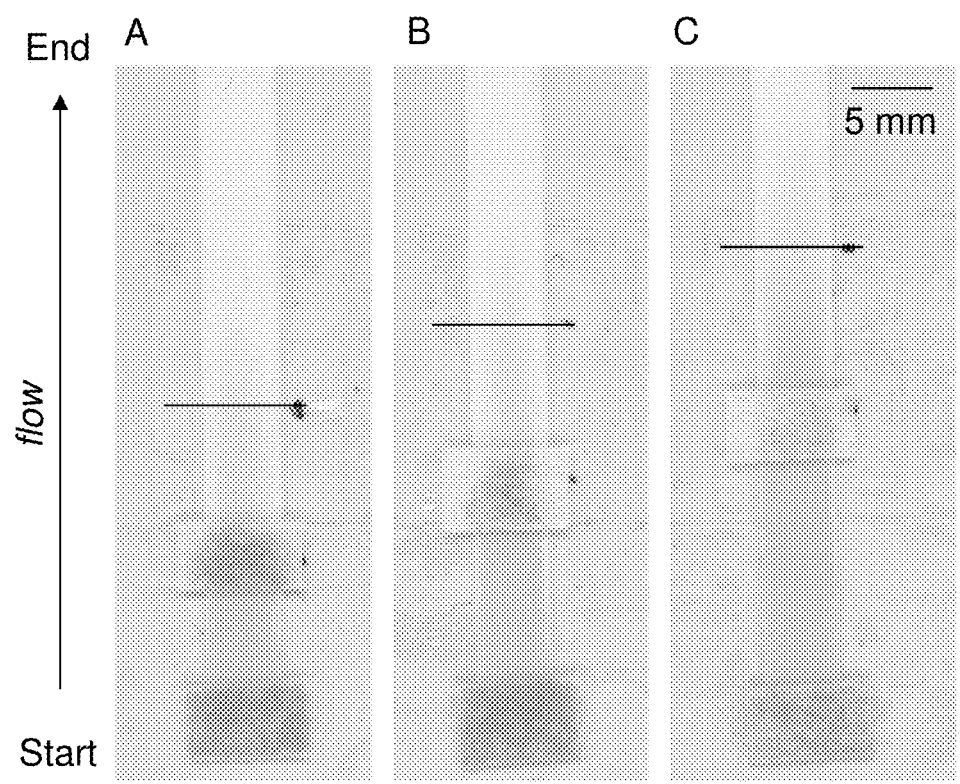
FIG. 5 demonstrates the moving of gold nanoparticle (GNP) with the fluid PBS along reagent flow path. The GNP and PBS fluid interface coverage was used to determine the optimal reagent pad separation distance. GNP and PBS fluid interface at designated point 10 mm past the upper source pad (black line) for varying source pad separation (Panel A) 10 mm source pad separation, PBS fluid front covers 58.18% of strip width at designated point (Panel B) 15 mm source pad separation, PBS fluid front covers 46.15% of strip width at designated point (Panel C) 20 mm source pad separation, PBS fluid front covers 90.00% of strip width at designated point.

FIG. 5 demonstrates the moving of gold nanoparticle (GNP) with the fluid PBS along reagent flow path. GNP and PBS fluid interface at designated point 10 mm past the upper source pad (black line) for varying source pad separation (Panel A) 10 mm source pad separation, PBS fluid front covers 58.18% of strip width at designated point (Panel B) 15 mm source pad separation, PBS fluid front covers 46.15% of strip width at designated point (Panel C) 20 mm source pad separation, PBS fluid front covers 90.00% of strip width at designated point. The test procedure is provided below.

Experimental Protocol:
1.) 5 mm×100 mm FF80HP nitrocellulose strips cut with Silhouette Studio scrapbook device
2.) 50 μL of blocking solution (5% sucrose, 2% BSA, 0.25% PVP, and 0.05% Tween in PBS) applied to strips and allowed to dry
3.) 5 mm×8 mm source pads cut from Millipore G041 glass fiber (GFCP1 030 00) and placed at the start of the strip and varying distances from the start of the strip (10 mm, 15 mm, 20 mm)
4.) Cellulose wick placed at the end of the nitrocellulose strip
5.) 25 μL of 1 OD streptavidin-poly HRP GNP deposited on upper source pad and 25 μL of PBS wash (with food coloring for visualization) placed on lower source pad simultaneously
6.) Flow timed until the front edge of the PBS reached 10 mm past the upper source pad
7.) Lateral flow strips imaged at time when front edge of PBS reached 10 mm past the upper source pad (to demonstrate "clean delivery", or highest percentage of PBS fluid front coverage at designated point)

Figure 6:
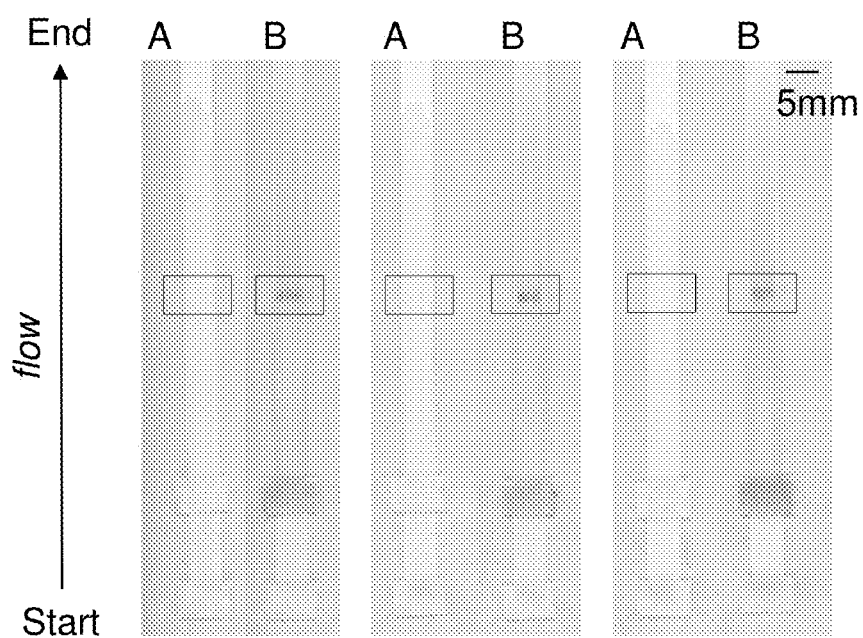
FIG. 6 demonstrates the importance of DAB amplification and the assay's consistency by three separate experiments. The one-dimensional lateral flow test with biotin control line was applied at the location indicated by the black box. Panel A shows the detection site after streptavidin-poly HRP GNP flow and panel B shows detection site after signal amplification with DAB reaction.

FIG. 6 demonstrates the importance of DAB amplification and the assay's consistency by three separate experiments. One-dimensional lateral flow test with biotin control line spotted at the location indicated by the black box. Panel A shows detection site after streptavidin-poly HRP GNP flow and panel B shows detection site after signal amplification with DAB reaction. The test procedure is found below.

Experimental Protocol:
1.) 5 mm×100 mm FF80HP nitrocellulose strips cut with Silhouette Studio scrapbook device
2.) 0.5 μL of biotinylated goat antibody (Thermo Fisher Scientific Ultra Vision Detection System, Anti-polyvalent, HRP/DAB, REF: TP-015-HD, LOT: PHD 151109) spotted at detection site, 45 mm above the start of the strip, and allowed to dry
3.) 50 μL of blocking solution (5% sucrose, 2% BSA, 0.25% PVP, and 0.05% Tween 20 in PBS) applied to strips and allowed to dry
4.) 5 mm×8 mm source pads cut from Millipore glass fiber and placed at the start of the strip and 15 mm above the start of the strip
5.) 2 cm×2.4 cm cellulose wick placed at the end of the nitrocellulose strip
6.) 25 μL of 1 OD streptavidin-poly HRP GNP deposited on upper source pad and 25 μL of PBS wash placed on lower source pad simultaneously
7.) Flow tests imaged after 5 minutes
8.) 25 μL of DAB deposited on upper source pad and 25 μL of PBS wash placed on lower source pad simultaneously
9.) Flow tests imaged after 10 minutes.

Figures 7A, 7B, 7C:
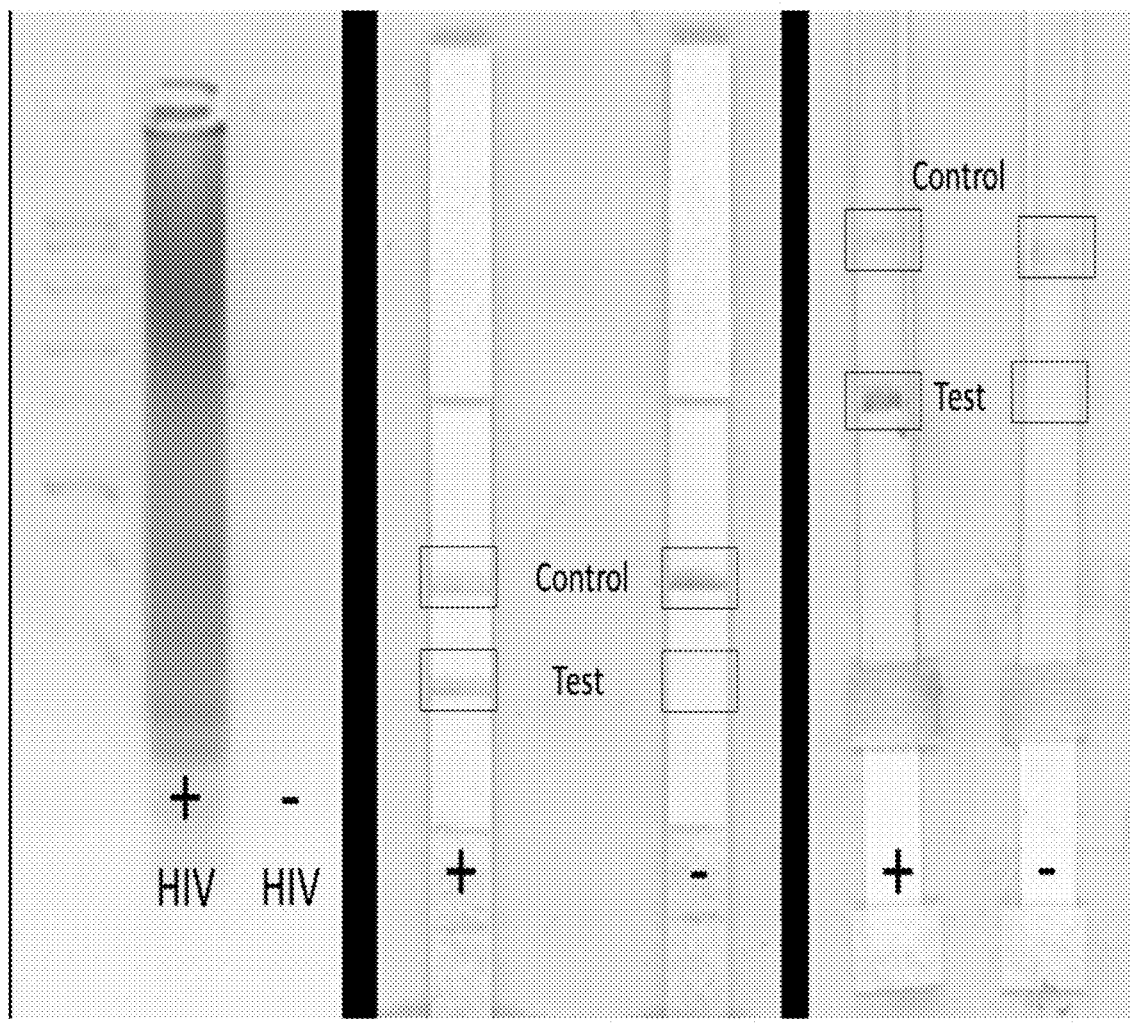
FIG. 7A demonstrates the validity of 1D- and 2DPN results as compared to results from positive and negative HIV LAMP samples on a gel electrophoresis. HIV LAMP samples tagged with FITC and biotin on 2% agarose gel: NEB fast ladder (left), 5 µL positive HIV LAMP sample (middle), and 5 µL negative HIV LAMP sample (right) (HIV: human immunodeficiency virus; LAMP: Loop Mediated Isothermal Amplification; RT-LAMP: Reverse transcription-Loop Mediated Isothermal Amplification).
FIG. 7B shows HIV LAMP samples tagged with FITC and biotin analyzed using commercial lateral flow strips with biotin control line and anti-FITC test line: negative HIV LAMP sample (right) and positive HIV LAMP sample (left).
FIG. 7C shows HIV LAMP samples tagged with FITC and biotin analyzed using our lab manufactured one-dimensional lateral flow test with biotin control line and anti-FITC test line: negative HIV LAMP sample after signal amplification with DAB reaction (right) and positive HIV LAMP sample after signal amplification with DAB reaction (left).

FIG. 7A shows HIV LAMP samples tagged with FITC and biotin on 2% agarose gel: NEB fast ladder (left), 5 μL positive HIV LAMP sample (middle), and 5 μL negative HIV LAMP sample (right) (HIV: human immunodeficiency virus; LAMP: Loop Mediated Isothermal Amplification; RT-LAMP: Reverse transcription-Loop Mediated Isothermal Amplification).

FIG. 7B shows HIV LAMP samples tagged with FITC and biotin analyzed using commercial lateral flow strips with biotin control line and anti-FITC test line: negative HIV LAMP sample (right) and positive HIV LAMP sample (left).

FIG. 7C shows HIV LAMP samples tagged with FITC and biotin analyzed using our lab manufactured one-dimensional lateral flow test with biotin control line and anti-FITC test line: negative HIV LAMP sample after signal amplification with DAB reaction (right) and positive HIV LAMP sample after signal amplification with DAB reaction (left). The test procedure is found below.

Figure 8A:
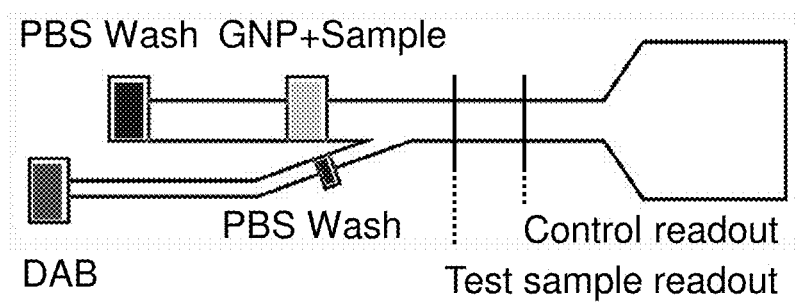
FIG. 8A shows the schematic of nitrocellulose 2DPN device with reagent source pads and detection lines.
Figure 8B:
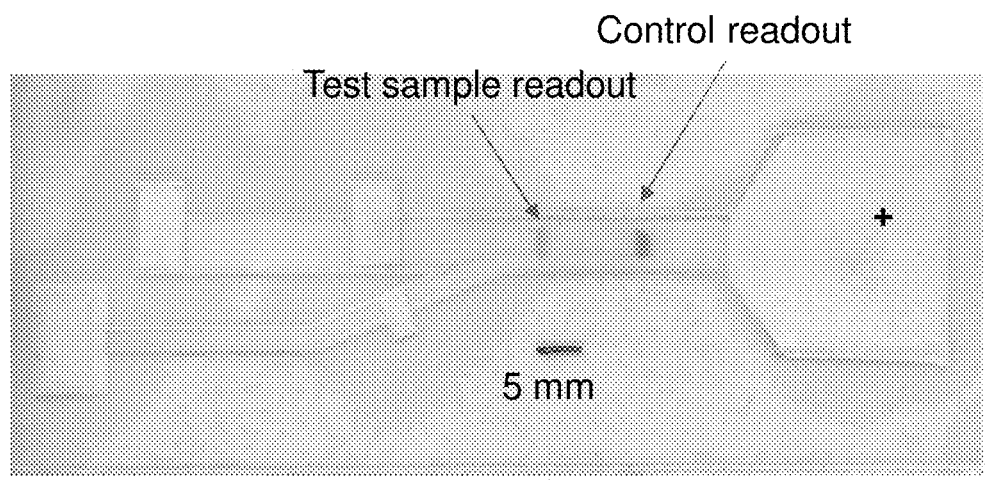
FIG. 8B shows the result of positive control HIV LAMP sample analysis using our lab-assembled 2DPN device disclosed herein.
Figure 8C:
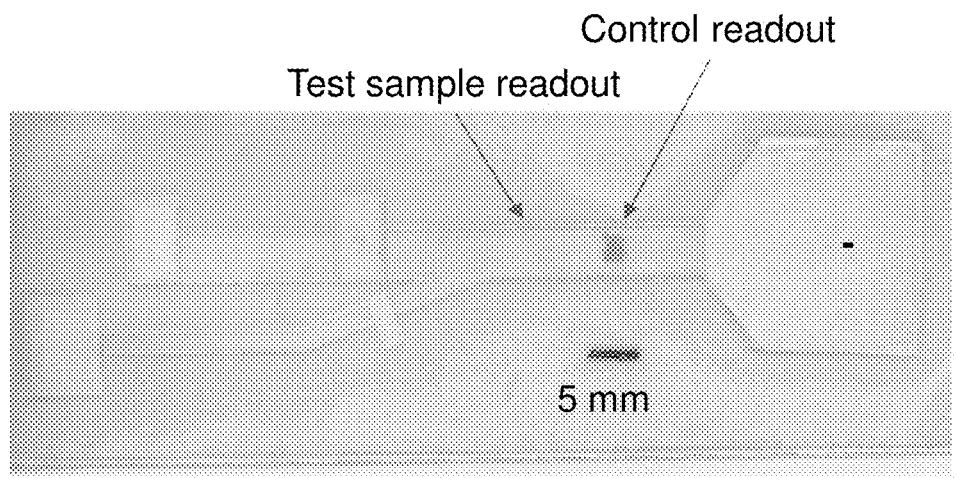
FIG. 8C shows the result of negative control HIV LAMP sample analysis using our lab-assembled 2DPN device disclosed herein.

Experimental Protocol:
1.) 5 mm×100 mm FF80HP nitrocellulose strips cut with Silhouette Studio scrapbook device
2.) 0.5 μL anti-FITC antibody (test line) spotted at detection site 35 mm above the start of the strip, and allowed to dry
3.) 0.5 μL of biotinylated goat antibody (control line) spotted at detection site, 45 mm above the start of the strip, and allowed to dry
4.) 50 μL of blocking solution (5% sucrose, 2% BSA, 0.25% PVP, and 0.05% Tween in PBS) applied to strips and allowed to dry
5.) 5 mm×8 mm source pads cut from Millipore glass fiber and placed at the start of the strip and 15 mm above the start of the strip
6.) 2 cm×2.4 cm cellulose wick placed at the end of the nitrocellulose strip
7.) 17 μL of 1 OD streptavidin-poly HRP GNP mixed with 7.84 μL of molecular bio water, and 0.16 μL of LAMP sample (1/50 dilution) in an Eppendorf tube. 25 μL sample mixture deposited on upper source pad and 25 μL of PBS wash placed on lower source pad simultaneously
8.) Flow tests imaged after 5 minutes
9.) 25 μL of DAB deposited on upper source pad and 25 μL of PBS wash placed on lower source pad simultaneously
10.) Flow tests imaged after 10 minutes FIG. 8A shows the schematic of nitrocellulose 2DPN device with locations of inputs and detection lines of control and test sample. FIG. 8B shows the result of +HIV LAMP sample analysis using our lab-assembled 2DPN device disclosed herein. FIG. 8C shows the result of −HIV LAMP sample analysis using our lab-assembled 2DPN device disclosed herein. The test procedure is found below.

Experimental Protocol:
1.) 2DPN designed using Adobe Illustrator
2.) 2DPN design cut from FF80HP nitrocellulose with Silhouette Studio scrapbook device 2.) 0.5 µL of biotinylated goat antibody spotted at detection site, 50 mm above the start of the strip, and allowed to dry
3.) 0.5 µL of anti-FITC antibody spotted at detection site, 40 mm above the start of the strip, and allowed to dry
4.) 75 µL of blocking solution (5% sucrose, 2% BSA, 0.25% PVP, and 0.05% Tween in PBS) applied to strips and allowed to dry
5.) 5 mm×8 mm source pads cut from Millipore glass fiber and placed at the start of the strip, 20 mm above the start of the strip, and at the start of the DAB leg
6.) 2 cm×2.4 cm cellulose wick placed at the end of the nitrocellulose strip
7.) 17 µL of 1 OD streptavidin-poly HRP GNP mixed with 7.84 µL of molecular bio water, and 0.16 µL of LAMP sample (1/50 dilution) in an Eppendorf tube. 25 µL sample mixture deposited on upper source pad and 25 µL of PBS wash placed on lower source pad, 5 µL PBS placed on upper source pad of DAB leg, 25 µL DAB placed on lower source pad of DAB leg
8.) Flow tests imaged after 5 minutes
9.) Flow tests imaged after 10 minutes Using the device disclosed herein, to carry out the assay, the end-user needs to remove the protective film covering the adhesive and add test sample and other reagents to the TARA reagent pads. Those reagents include FITC and biotin tags, and phosphate buffer containing 0.5%. By folding the 2DPN card, the assay flow is activated, and the FITC tag of the TARA amplicons will bind to the anti-FITC patterned detection line. Signal amplification result from streptavidin-HRP conjugated nanoparticles (Cytodiagnostics, Burlington, OT) binds to the biotinylated end of the amplicon concentrated at the detection line and the subsequent colorimetric precipitation reaction with DAB (3,3'-diaminobenzidine tetrahydrochloride)/peroxide substrate. The biotinylated secondary antibodies have been spotted onto the nitrocellulose strip as a positive control line to bind to excess streptavidin-HRP conjugates and react with the DAB/peroxide substrate. The template-assisted acyl transfer reaction conditions between G-probe and A-probe at various loads of template RNA as shown in FIGS. 4A and 4B may need some further optimization.

While the time delay conserves materials and time, the mixer wherein all reagents are fully mixed enable the test to its full potential. If only the time delay component were in place without the mixer, the three reagents would segregate into parallel channels across the width of the device, impairing or completely eliminating the reaction. The reaction requires all three reagents to flow across the width of the detection area sequentially. With three parallel flow lines, the sequential reaction would not occur between reagents, causing the test to fail. This was a challenge observed before trying various mixing and turbulence-inducing techniques to the flow pattern.

If the mixer was implemented without the time delay, the third reagent, chromogen (e.g. DAB, 3,3'-diaminobenzidine tetrahydrochloride), would flow before or around the same time as the first and second reagents. The multi-step amplification reaction would not occur. An alternative potential solution to this would be to significantly lengthen the third reagent (DAB) leg of the device (estimate on the order of centimeters) which would use more materials (paper, plastics, packaging, etc.) to make the device, lead to a much bigger device, and require a significantly longer time to run the test. Another complication is that the other reagents would spread out in every available direction.

As the first and second reagent begin to flow, they will be naturally wicked into the DAB leg of the device, as well as the desired central channel. This introduces a large amount of background noise around the mouth of this leg of the device, due to the reaction between the first (streptavidin HRP) and third (DAB) reactants. If background reactions were to occur in this area, the tests would fail because the active DAB would never reach the detection area for signal amplification. Similarly, the first and second reagent flowing up this channel impede the capillary action, which is acting on the third reagent in the dry channel to pull it to the central channel.

The improved 2DPN maintains its positive aspects of conventional lateral flow tests (e.g. pregnancy test) for point-of-care while increasing the control over timing and sample delivery, improved detection capability, and signal enhancement. This improved device may find uses in analysis of toxic contaminants in agricultural and food products, and may provide a useful tool for clinical diagnosis at the point of care.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The invention claimed is:

1. A method for reducing smears and improving sharpness and intensity of test readout of a chemical assay or immunoassay, the method comprises providing a time delay pad (2) operably positioned before where a third reagent pad (5) merges into a second reagent pad (4) on a reagent flow path (7) on a paper-based analytical device, wherein said paper-based analytical device comprises
   a) two pieces of supporting plates,
      on the first piece of said supporting plates is a paper strip of porous media comprising a plurality of extended legs centered around a reagent flow path (7), a curved mixer (1) before a readout region (9) preloaded with visualizing reagents for the test sample and its control, and a head of a relatively large size;
   and
      on the second piece of said supporting plates are a plurality of absorbent pads comprising a time-delay pad (2), a pad (3) for the test sample and a first reagent, a pad (4) for a second reagent or optionally for buffer, a pad (5) for a third reagent of an enzymatic substrate or additional signal amplification, and a wicking pad (6) relatively large in size, wherein each of said absorbent pads are spatially placed for covering and connecting with a respective one of the extended legs and the wick head of the paper strip on the first piece of supporting plate; wherein said time delay pad (2) is placed on the leg of the third reagent pad (5) before it merges onto a reagent flow path (7) of the first supporting plate, whereby reagent flowing from the first reagent pad (3), the second reagent pad (4), and the third reagent (5) are initiated at the same time but arrives sequentially at said readout region (9) once the two pieces of supporting plates are folded together;

b) a plurality of testing reagents; and c) a test card that holds components of a) and b).

2. The method according to claim 1, further comprises omitting a curved mixer (1) operably positioned before the region for test sample readout region (9) to the paper-based analytical device.

3. The method according to claim 1, wherein said curved mixer (1) comprises a U-shaped, a zig-zag, a square-wave, or a serpentine component wherein sufficient mixing and interactions of testing reagents with a testing sample are achieved.

4. The method according to claim 1, wherein said paper-based analytical device is a device suitable for a point-of-care chemical assay or immunoassay of a test sample.

5. A method for reducing smears and improving sharpness and intensity of test readout of a chemical assay or immunoassay, comprising providing a curved mixer (1) operably positioned before a test sample readout to a paper-based analytical device, wherein said curved mixer comprises a U-shaped, a zig-zag, a square-wave, or a serpentine component wherein sufficient mixing and interactions of testing reagents with a testing sample are achieved in a way that reduces smears and improves sharpness and intensity of the test readout, further comprising providing a time delay pad (2) operably positioned before where a third reagent from pad (5) merges into a second reagent from pad (4) on a reagent flow path (7).

6. The method according to claim 5, wherein said paper-based analytical device is a device suitable for a point-of-care chemical assay or immunoassay of a test sample.

7. A method for reducing smears and improving sharpness and intensity of test readout of a chemical assay or immunoassay, comprising providing a curved mixer (1) operably positioned before a test sample readout to a paper-based analytical device, wherein said curved mixer comprises a U-shaped, a zig-zag, a square-wave, or a serpentine component wherein sufficient mixing and interactions of testing reagents with a testing sample are achieved; and providing a time delay pad (2) operably positioned before where the third reagent from pad (5) merges into a second reagent from pad (4) on a reagent flow path (7), wherein said paper-based analytical device comprises a) two pieces of supporting plates,
on the first piece of said supporting plates is a paper strip of porous media comprising a plurality of extended legs centered around the reagent flow path (7), and in the flow path (7) a curved mixer (1) before a readout region (9) preloaded with visualizing reagents for the test sample and its control, and a head of a relatively large size; and on the second piece of said supporting plates are a plurality of absorbent pads comprising a time-delay pad (2), a pad (3) for the test sample and a first reagent, a pad (4) for a second reagent or buffer, a pad (5) for a third reagent of an enzymatic substrate or additional signal amplification, and a wicking pad (6) of relatively large in size, wherein each of said absorbent pads are spatially placed for covering and connecting with a respective one of the extended legs and the wick head of the paper strip on the first piece of supporting plate; wherein said time delay pad (2) is placed on the leg of the third reagent pad (5) before it merges onto the reagent flow path (7) of the first supporting plate, whereby reagent flowing from the first reagent pad (3), the second reagent pad (4), and the third reagent (5) are initiated at the same time but arrives sequentially at said readout region (9) once the two pieces of supporting plates are folded together;

b) a plurality of testing reagents; and c) a test card that holds components of a) and b).

8. The method according to claim 7, wherein said curved mixer (1) comprises a U-shaped, a zig-zag, a square-wave, or a serpentine component wherein sufficient mixing and interactions of testing reagents with a testing sample are achieved.

9. The method according to claim 7, wherein said paper-based analytical device is a device suitable for a point-of-care chemical assay or immunoassay of a test sample.

10. The method according to claim 7, wherein said first reagent for sample binding and signal amplification are selected from the group consisting of silver nanoparticles, gold nanoparticles, polystyrene microbeads, and latex microbeads, with or without a detection analyte attached.

11. The method according to claim 7, wherein said first reagent is coated with an enzyme selected from the group consisting of horseradish peroxidase, alkaline phosphatase, glucose oxidase, and beta-galactosidase.

12. The method according to claim 7, wherein said first reagent comprises a detection analyte selected from the group consisting of streptavidin, antibody, antigen, or a nucleic acid sequence, and an enzyme.

13. The method according to claim 7, wherein said first reagent is solid or lyophilized, and rehydrated upon use.

14. The method according to claim 7, wherein said first reagent for sample binding and signal amplification is supplied as separate wet reagents.

15. The method according to claim 7, wherein said third reagent of an enzymatic substrate for horseradish peroxidase-based detection is selected from the group consisting of 3,3',5,5'-tetramethylbenzidine, o-phenylenediamine dihydrochloride, 3,3'-diaminobenzidine, 2,2'-Azinobis [3-ethylbenzothiazoline-6-sulfonic acid], and 4-chloro-1-naphthol.

16. The method according to claim 7, wherein said third reagent for additional signal amplification comprises a silver salt, an initiator, or a fixer.

17. The method according to claim 7, wherein said paper stripe is nitrocellulose treated with a blocking reagent selected from the group consisting of serum albumin, polyvinyl pyrrolidone, polysorbates, and sugar.

18. The method according to claim 7, wherein said absorbent pads are an absorbent material selected from the group consisting of glass fiber, bound glass fiber, cellulose, and derivatives thereof.

19. The method according to claim 18, wherein said absorbent material are treated with a blocking reagent comprising serum albumin, polyvinyl pyrrolidone, polysorbates, and sugar.

* * * * *